United States Patent [19]

Butterworth et al.

[11] Patent Number: 5,648,141

[45] Date of Patent: Jul. 15, 1997

[54] DEBRIDEMENT SPONGE

[75] Inventors: David E. Butterworth, Colleyvile, Tex.; John Dyer, Randolph; John W. Kennette, Somerville, both of N.J.

[73] Assignee: Chicopee, New Brunswick, N.J.

[21] Appl. No.: 501,360

[22] Filed: Jul. 12, 1995

Related U.S. Application Data

[63] Continuation of Ser. No. 308,108, Apr. 19, 1994, abandoned, which is a continuation of Ser. No. 823,235, Jan. 21, 1992, abandoned.

[51] Int. Cl.$^6$ ..................................................... B32B 3/10
[52] U.S. Cl. .......................... 428/131; 428/134; 604/358
[58] Field of Search ...................................... 428/131, 255, 428/299, 134; 604/358

[56] References Cited

U.S. PATENT DOCUMENTS 5,098,764  3/1992  Drelich et al. ........................... 428/131

Primary Examiner—Christopher Raimund

[57] ABSTRACT

A debridement sponge made from a nonwoven fabric comprising, in a preferred form, yarn-like strands of bleached cotton fibers. In the preferred form, the strands are interconnected at multiple junctures to form fewer than 31 generally rectangular apertures per cm$^2$. Moreover, each aperture has an area of 1.3 mm$^2$. Furthermore, the fabric has a Calculated Strand Density of 0.171 g/cc, a Clarity Index of at least 0.75, and an Absorbent Capacity of at least 7 grams of a colored, aqueous, saline solution per gram of the fabric when compressed under a pressure of 3.3 g/cm$^2$. Plug Harshness and Compression Recovery of the fabric are excellent.

15 Claims, 11 Drawing Sheets

DEBRIDEMENT SPONGE

This is a continuation of application Ser. No. 08/308,108, filed Apr. 19, 1994, now abandoned, which is a continuation of Ser. No. 07/823,235, filed Jan. 21, 1992, now abandoned, both of which are hereby incorporated by reference.

TECHNICAL FIELD OF THE INVENTION

This invention pertains to a debridement sponge useful in the management of an acute or chronic wound. The sponge is made from a novel, apertured, nonwoven fabric comprising bundled strands of fibers including hydrophilic fibers, such as cotton fibers, which may be blended with hydrophobic fibers for some applications. The fabric provides the sponge with superior packing and debridement capabilities believed to result at least in part from the Absorbent Capacity, Clarity Index, and Calculated Strand Density of the fabric. Absorbent Capacity, Clarity Index, and Calculated Strand Density are fabric properties determinable as specified hereinafter.

BACKGROUND OF THE INVENTION

Packing and debridement are extensively practiced for the management of acute and chronic wounds. Presenting a clean wound free from necrotic tissue, slough, and eschar that would interfere with repair is a most important preparatory step for effective wound healing. The removal of nonviable material reduces the incidence of infection and facilitates healing through the formation of healthy granulation tissue and through re-epithelization.

Packing refers to the filling of a wound or cavity with a sponge or other material. Packing is used to absorb excess wound exudate, along with any bacteria present therein, and to facilitate the formation of granulation tissue. Debridement refers to the removal of necrotic tissue from the wound site until healthy tissue is exposed.

The primary objectives of debridement are to encourage granulation and to prevent infection. A freshly debrided wound will express considerable amounts of serous fluid from the denuded cells. Granulation can be encouraged by preventing such fluid from accumulating and reclotting in the wound.

Various methods of debridement are known. These methods include surgical debridement, liquefaction through autolysis or with the aid of added enzymes, and mechanical debridement wherein the endogenous material is scrubbed or pulled away from the wound by means of a sponge or dressing. The procedure selected by the physician depends on numerous factors including the nature of the wound, the condition of the patient, and the situation in which the wound is presented for management.

The use of gauze sponges woven from bleached cotton yarn for packing and debriding wounds is widely practiced. When applied, such sponges are wetted with saline or other prescribed solutions. Such sponges are believed to be effective for mechanical debridement because their densely packed, twisted fiber, yarn elements in the wet state conform freely to the wound topography and upon partially drying embed themselves in or otherwise attach themselves to the necrotic tissue. When the partially dry sponge is removed, the necrotic tissue adhering thereto is also removed. Under some conditions, woven cotton gauze can be too aggressive so that trauma can result if such gauze is allowed to dry completely before it is removed. Often, to prevent excessive disruption of newly formed granulation tissue, woven cotton gauze is not allowed to dry completely or is redampened prior to its removal.

Typically, a sponge made from woven cotton gauze has multiple plies, e.g. twelve plies, with 20×8 yarns per square inch in each ply, so as to provide void volume for holding viscous, purulent exudate. Including the spaces between the plies and the large apertures, such a sponge has a rather limited void volume in which to store wound exudate. However, its highly twisted yarns are effective in wicking and lateral transport of liquids and suspended solids.

Altogether, for the management of acute and chronic wounds, woven cotton gauze has significant limitations. As noted above, such gauze can be too aggressive and is not selective in its adherence to material at the surface of the wound. Moreover, such gauze can shed yarn fragments and particles when opened and unfolded, and especially when cut. Such fragments and particles can contaminate the wound and can be very difficult to remove. Furthermore, being woven from twisted yarns, such gauze has relatively low absorptive capacity. Under some conditions, woven cotton gauze can become wadded in a deep, cavernous, undermined wound.

Nonwoven fabrics, made from entangled fibers, have become widely accepted for use as wound dressings and bandages because of their qualities of absorbent capacity, softness, bulk, low linting, and ease of removal from wounds. Nonwoven fabrics of a type known as spunlace fabrics have been widely accepted for general use sponges, wound dressings, and bandages. Typically, spunlace fabric sponges are made from rayon fibers or blends of rayon and polyester fibers. Spunlace fabrics are exemplified in Buyofsky et al. U.S. Pat. No. 4,693,922 and U.S. Pat. No. 4,735,842.

In contrast with woven gauze sponges, spunlace fabric sponges known heretofore are typically comprised of low density strands and have "cloudy", i.e. indistinct, apertures. When wet, the strands of spunlace fabric sponges known heretofore do not conform readily to the wound surface. Upon drying, such strands do not become as deeply embedded in or as firmly attached to necrotic tissue. Thus, when removed, spunlace fabric sponges known heretofore are less aggressive and may be not entirely effective in removing eschar and necrotic debris. Including their inter-ply spaces, cloudy apertures, and low density strands, spunlace fabric sponges have substantially greater void volumes, as compared to the rather limited void volumes of woven gauze sponges. However, spunlace fabric sponges known heretofore have rather low ability to mechanically debride necrotic tissue.

Despite its limitations, and particularly as compared to spunlace fabrics known heretofore, woven cotton gauze has remained a preferred material for sponges used to pack and debride wounds.

There has been a need, to which this invention is addressed, for a debridement sponge combining the best features of woven gauze sponges and spunlace fabric sponges known heretofore without the significant limitations of either.

SUMMARY OF THE INVENTION

This invention provides a novel sponge having superior packing and debridement capabilities when compared to woven gauze sponges, to spunlace fabric sponges known heretofore, and to other fabric sponges known heretofore. The novel sponge is made from a novel, nonwoven, apertured fabric comprising bundled strands of hydrophilic fibers, such as bleached cotton fibers, which may be blended with hydrophobic fibers, such as polyester fibers, for some applications. The strands are interconnected at multiple junctures to form multiple apertures, which may be generally rectangular or otherwise shaped. It is presently preferred that the fabric be free of binder compositions. As explained below, it is believed that the Absorbent Capacity, Clarity Index, and Calculated Strand Density of the nonwoven fabric contribute to the superior capabilities of the novel sponge. As used herein, "Absorbent Capacity", "Clarity Index", and "Calculated Strand Density" refer to fabric properties determinable as specified hereinafter.

The novel sponge combines the best features of woven gauze sponges and spunlace fabric sponges without the significant limitations of either. When wet, the novel sponge conforms to the wound surface and becomes well embedded in or firmly attached to the necrotic tissue, much in the same way as woven gauze conforms and becomes embedded. Viscous fluids flow freely into the void volume of the sponge. Also, the strands adhere to the necrotic tissue, which is removed with the sponge. As compared to spunlace fabric sponges, sponges according to this invention have more three dimensional surfaces, so as to have a lower bulk density when plied up. Also, as compared thereto, sponges according to this invention have a greater absorbent capacity.

For mechanical debridement, the novel sponge is uniquely effective. If it is made wholly from cotton fibers, it compares favorably to a woven cotton gauze sponge. For packing in situations where absorbent capacity before, during, and after compression is important, the novel sponge is superior to a woven gauze sponge. Although it is preferred to make the sponge wholly from cotton fibers, for enhanced absorbent capacity the sponge can be made from blended cotton and polyester fibers for situations where less aggressive mechanical debridement or even greater absorbent capacity is preferred. As compared to cotton fibers, polyester fibers tend to be more resilient when wet, which may be desirable for some applications, as with deep, cavernous, undermined wounds that may be difficult to pack. The inclusion of a portion of polyester fibers provides a sponge which tends to resist "hardening" during use.

The superior capabilities of the novel sponge provided by this invention are believed to result at least in substantial part from the Absorbent Capacity, Clarity Index, and Calculated Strand Density of its novel, nonwoven, apertured fabric. While formation from bleached cotton fibers is presently most preferred, other types of fibers may be blended with cotton fibers, or alternately employed. Irrespective of the fiber content, fabrics used for forming sponges according to this invention minimally exhibit an Absorbent Capacity of at least 5 grams of a colored, aqueous, saline solution per gram of the fabric when compressed under a pressure of 3.3 grams per square centimeter, a Clarity Index of at least 0.4, and a Calculated Strand Density of at least 0.11 grams per cubic centimeter. Absorbent Capacity is determinable by means of a gravimetric absorbency tester to be later described. The colored, aqueous, saline solution is to be later specified. Clarity Index and Calculated Strand Density are determined by test methods to be later described.

It is desirable for the Absorbent Capacity, Clarity Index, and Calculated Strand Density to be notably greater than those values noted in the preceding paragraph. The Absorbent Capacity is preferably at least 6.0 grams of the colored, aqueous, saline solution per gram of the fabric when compressed at a pressure of 3.3 grams per square centimeter, and most preferably 7.0 grams of the colored, aqueous, saline solution per gram of the fabric at such a pressure. The Clarity Index is preferably at least 0.5, and most preferably at least 0.75. The Calculated Strand Density is preferably at least 0.14 grams per cubic centimeter, and most preferably at least 0.17 grams per cubic centimeter.

It is useful to compare the Absorbent Capacity, Clarity Index, and Calculated Strand Density of woven cotton gauze. In representative values, woven cotton gauze has an Absorbent Capacity of 3.8 grams of the colored, aqueous, saline solution per gram of such gauze when compressed under a pressure of 3.3 grams per square centimeter, a Clarity Index of 1.30, and a Calculated Strand Density of 0.35 grams per cubic centimeter.

"Plug Harshness" refers to the compressibility of a sponge and to its absorbency when compressed. The fabric of the novel sponge is compressible to a thickness equal to one half of its initial wet thickness, under a pressure of less than 296 grams per square centimeter, with a residual Absorbent Capacity of at least 2.5 grams of the colored, aqueous, saline solution per gram of the fabric when so compressed. In other words, the fabric is first saturated, then compressed to one half of its initial wet thickness, and the remaining liquid is determined. The initial wet thickness is determined when the fabric is compressed under a pressure of 3.3 grams per square centimeter. These parameters define the Plug Harshness of the sponge.

"Compression Recovery", a term related to Plug Harshness, refers to the absorbency of the sponge after the pressure has been reduced. Minimally, after the pressure is reduced to a pressure of 3.3 grams per square centimeter, such fabric has an Absorbent Capacity of at least 4.0 grams of the colored, aqueous, saline solution per gram of the fabric. These parameters define the Compression Recovery of such fabric.

While the above parameters for Plug Harshness and Compression Recovery have been determined to be those that are considered to be minimally acceptable, the most preferred forms of the present sponge exhibit more desirable values for these performance characteristics.

Preferably, the fabric of the novel sponge is compressible to a thickness equal to one half of its initial wet thickness determined as noted above, under a pressure of less than 247 grams per square centimeter, with an Absorbent Capacity of at least 3.0 grams of the colored, aqueous, saline solution per gram of the fabric when so compressed. After the pressure is reduced to 3.3 grams per square centimeter, such fabric then should have an Absorbent Capacity of at least 4.5 grams of such solution per gram of the fabric.

Most preferably, the sponge is formed from fabric which is compressible to a thickness equal to one half of its initial wet thickness determined as noted above, under a pressure of less than 222 grams per square centimeter, with an Absorbent Capacity of at least 3.25 grams of the colored, aqueous, saline solution per gram of the fabric. After the pressure is reduced to 3.3 grams per square centimeter, such fabric then should have an Absorbent Capacity of at least 5.0 grams of such solution per gram of the fabric.

Desirably, each aperture is generally rectangular. It is desirable for each such aperture to have an area greater than at least 0.6 square millimeters and for there to be fewer than 77.5 apertures per square centimeter. Preferably, each such aperture has an area of at least 1.0 square millimeters, and the apertures number fewer than 46.5 per square centimeter. Most preferably, each such aperture has an area of at least 1.3 square millimeters, and the apertures number fewer than 31 per square centimeter.

The strand fibers may be hydrophilic fibers, preferably free of leachable materials, preferably bleached cotton fibers. Such hydrophilic fibers may be blended with hydrophobic fibers, such as polyester fibers [e.g. poly(ethylene terephthalate) fibers] for some applications.

These and other objects, features, and advantages of this invention are evident from the following description of a preferred embodiment of this invention with reference to the accompanying drawings.

DETAILED DESCRIPTION OF PREFERRED EMBODIMENT

Figure 1:
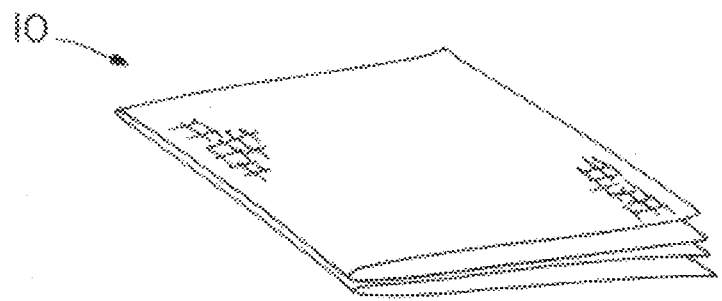
FIG. 1 is a perspective view of a four-ply sponge according to this invention, as made from a novel, nonwoven, apertured fabric.
Figure 2:
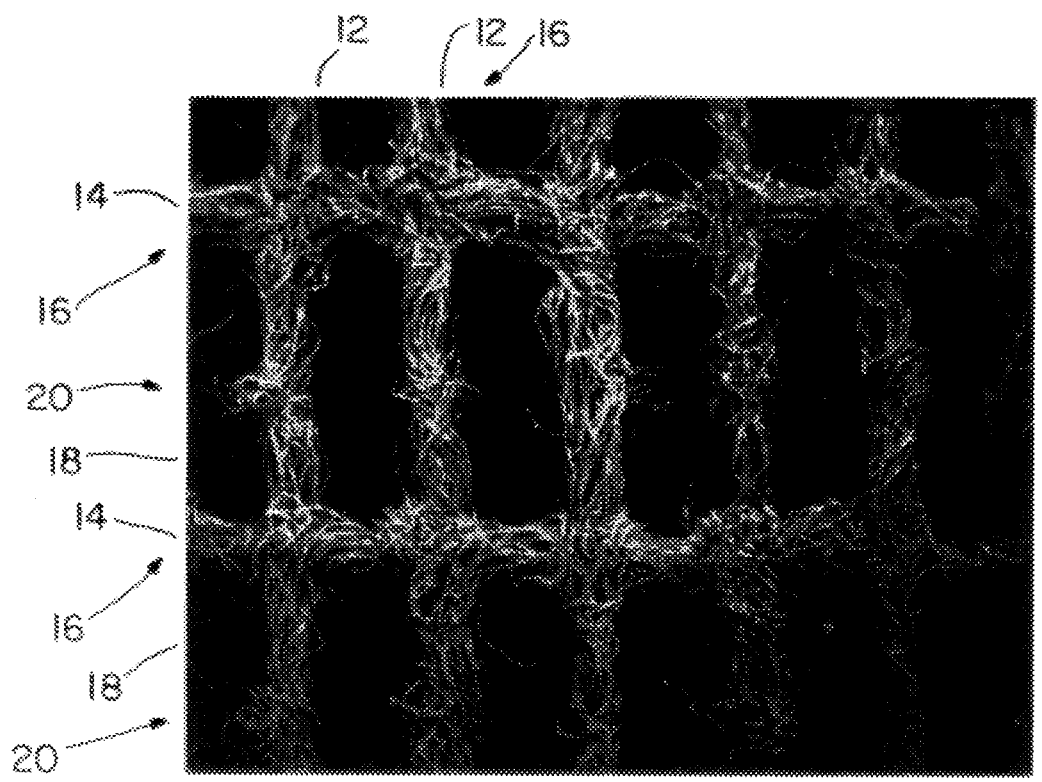
FIG. 2, on a greatly enlarged scale, is a photomicrograph of a representative area of a sample of an apertured fabric useful to make sponges according to this invention.

As shown in FIG. 1, a debridement sponge 10 constitutes a preferred embodiment of this invention. The sponge 10 is made by folding a square piece of the novel, apertured, nonwoven fabric into four plies. Typically, the folded sponge measures 4 inches×4 inches. It will be understood that the sponge may have a different number of plies and different dimensions. As shown in FIG. 2, the fabric comprises bundled strands of fibers, namely longitudinal strands 12 and transverse strands 14. Preferably, the fibers are bleached cotton fibers. The longitudinal and transverse strands 12, 14, are interconnected at multiple junctures 16 to form multiple, generally rectangular apertures 18. The longitudinal strands 12 extend generally in the machine direction. The transverse strands 14 extend generally in the cross-machine direction. Each of the bundled strands 12, 14, is comprised of densified, compacted, fiber segments, many of which fiber segments are parallel to one another. Between the junctures 16 at the longer sides of the apertures 18, the fibers may be further entangled and to be circumferentially wrapped around the peripheries of the fiber segments so as to form so-called "bow tie" configurations 20.

Combining the best features of woven gauze sponges and spunlace fabric sponges without the significant limitations of either, the sponge 10 has superior packing and debridement capabilities when compared to sponges known heretofore. These superior capabilities are believed to result at least in part from the Absorbent Capacity, Clarity Index, and Calculated Strand Density of the fabric of the sponge 10.

A highly desirable feature of the sponge of the present invention relates to its ability to be cut with minimal particulate matter being created. The presence of such particulate matter is undesirable for wound treatment. Testing has shown that cutting of woven cotton gauze may create as much as twelve times the wet particulate matter as exists with uncut gauze (on a weight basis). Significantly, by virtue of its nonwoven nature, sponges formed in accordance with the present invention, when cut, create as little as twice the wet particulate matter as exists with the uncut sponges.

Minimally, the fabric of the sponge 10 has an Absorbent Capacity of at least 5 grams of a colored, aqueous, saline solution specified hereinafter per gram of the fabric when compressed under a pressure of 3.3 grams per square centimeter of the fabric, a Clarity Index of at least 0.4, and a Calculated Strand Density of at least 0.11 grams per cubic centimeter. Preferably, the fabric of the sponge 10 has an Absorbent Capacity of at least 6 grams of the colored, aqueous, saline solution per gram of the fabric when compressed under a pressure of 3.3 grams per square centimeter of the fabric, a Clarity Index of at least 0.5, and a Calculated Strand Density of at least 0.14 grams per cubic centimeter. Most preferably, the fabric of the sponge 10 has an Absorbent Capacity of at least 7 grams of the colored, aqueous, saline solution per gram of the fabric when compressed under a pressure of 3.3 grams per square centimeter of the fabric, a Clarity Index of at least 0.75, and a Calculated Strand Density of at least 0.17 grams per cubic centimeter.

The Plug Harshness and Compression Recovery of the fabric of the sponge 10 are excellent. Minimally, the fabric of the sponge 10 is compressible to a thickness equal to one half of its initial wet thickness, under a pressure of less than 296 grams per square centimeter, and when so compressed has an Absorbent Capacity of at least 2.5 grams of the colored, aqueous, saline solution per gram of the fabric. After the pressure is reduced to a pressure of 3.3 grams per square centimeter, the fabric 10 then has an Absorbent Capacity of at least 4.0 grams of the colored, aqueous, saline solution per gram of the fabric. The initial wet thickness is determined under a pressure of 3.3 grams per square centimeter.

Preferably, the fabric of the sponge 10 is compressible to a thickness equal to one half of its initial wet thickness determined as noted above, under a pressure of less than 247 grams per square centimeter, with an Absorbent Capacity of at least 3.0 grams of the colored, aqueous, saline solution per gram of the fabric. After the pressure is reduced to a pressure of 3.3 grams per square centimeter, the fabric 10 then has an Absorbent Capacity of at least 4.5 grams of the colored, aqueous, saline solution per gram of the fabric 10.

Most preferably, the fabric of the sponge 10 is compressible to a thickness equal to one half of its initial wet thickness determined as noted above, under a pressure of less than 222 grams per square centimeter, with an Absorbent Capacity of at least 3.25 grams of the colored, aqueous, saline solution per gram of the fabric. After the pressure is reduced to a pressure of 33.3 grams per square centimeter, the fabric 10 then has an Absorbent Capacity of at least 5.0 grams of the colored, aqueous, saline solution per gram of the fabric 10.

Minimally, each generally rectangular aperture 18 has an area of at least 0.6 square millimeters, and the apertures 18 number fewer than 77.5 per square centimeter. It is desirable for each such aperture to have a greater area and for there to be even fewer apertures per square centimeter. Preferably, each such aperture 18 has an area of at least 1.0 square millimeters, and the apertures 18 number fewer than 46.5 per square centimeter. Most preferably, each such aperture 18 has an area of at least 1.3 square millimeters, and the apertures 18 number fewer than 31 per square centimeter.

Production Process

Except as illustrated and described herein, the preferred process for producing the novel, apertured, nonwoven fabric used to make sponges according to this invention is similar to the process disclosed in a U.S. Pat. No. 5,098,764 as filed Mar. 12, 1990, under Ser. No. 07/491,797, for NON-WOVEN FABRIC AND METHOD AND APPARATUS FOR MAKING THE SAME, the disclosure of which is incorporated herein by reference. Further details of the preferred process therefor may be thus supplied by reference to this copending application.

As used herein, the term fabric refers to a web of fibers held together with sufficient integrity so as to be self-supporting. While it is presently preferred that the fabric employed for forming the present debridement sponge be free of binder compositions, it may be desirable to employ such compositions for some applications.

Figure 3:
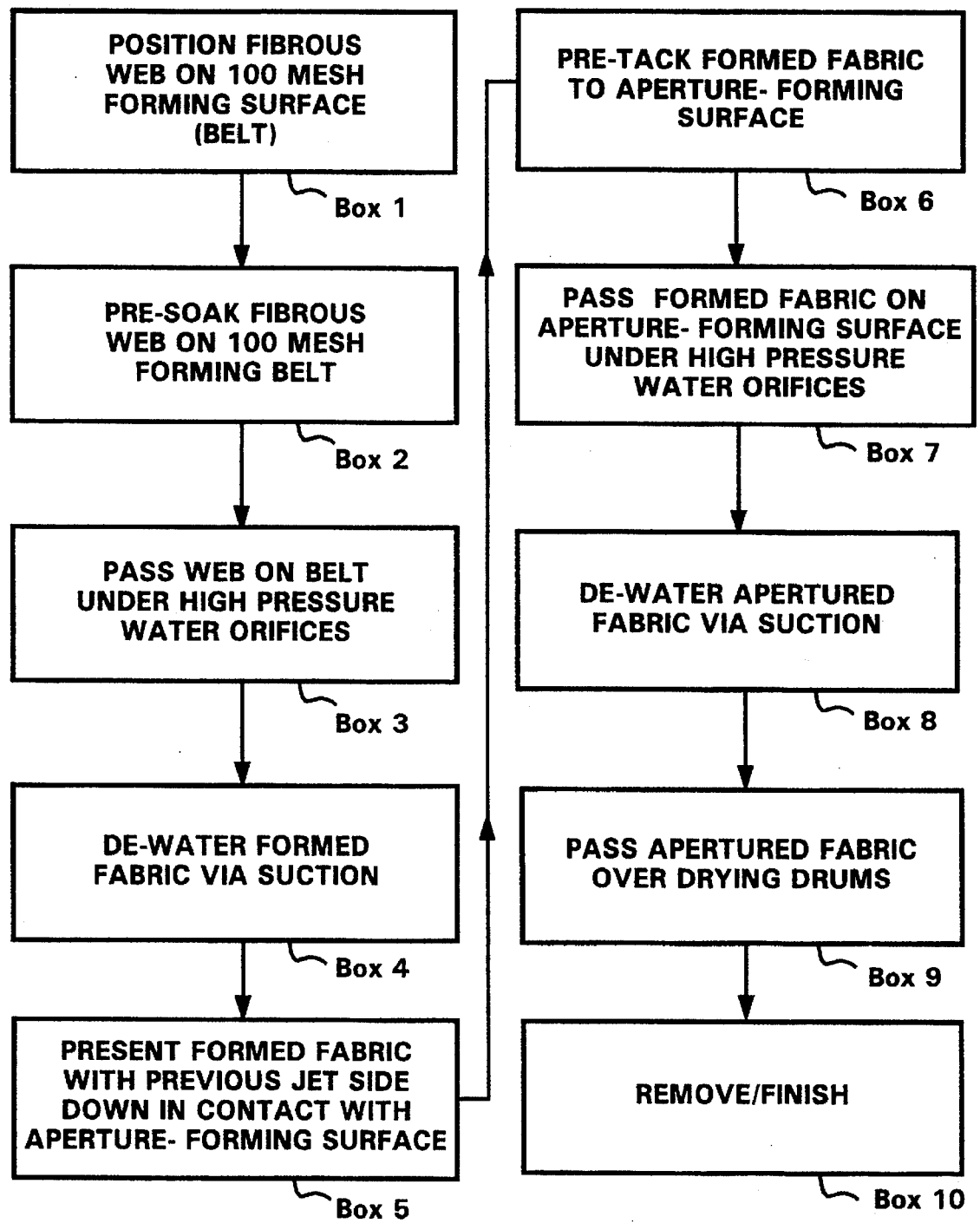
FIG. 3 is a block diagram of one contemplated process for making such an apertured fabric.

FIG. 3 is a block diagram showing successive steps in the preferred process noted above. The first step in this process is to position a web of fibers on a foraminous (e.g. 100 mesh) support member (Box 1) of a first entangler. The fibrous web is pre-soaked or wetted out while on this support member (Box 2) to ensure that as it is being treated it will remain on the support member. The support member with the fibrous web thereon is passed under high pressure fluid-ejecting orifices (Box 3). The preferred fluid is water. Excess water is removed from the formed fabric, preferably using a vacuum (Box 4). The formed fabric is disengaged from the 100 mesh support member of the first entangler and is presented to a topographical, aperture-forming surface of a second entangler, so that the entangled side previously contacted by water jets is now in contact with the aperture-forming surface (Box 5). Water is applied to the formed fabric to tack such fabric onto the aperture-forming surface (Box 6). The aperture-forming surface with the formed fabric thereon is passed under high pressure fluid-ejecting orifices (Box 7) to form an apertured fabric. Again the preferred fluid is water. Residual water is removed from the apertured fabric (Box 8). The apertured fabric is passed over a series of drying drums to dry such fabric (Box 9). The dried fabric may be then finished or otherwise processed as desired (Box 10).

Figure 4:
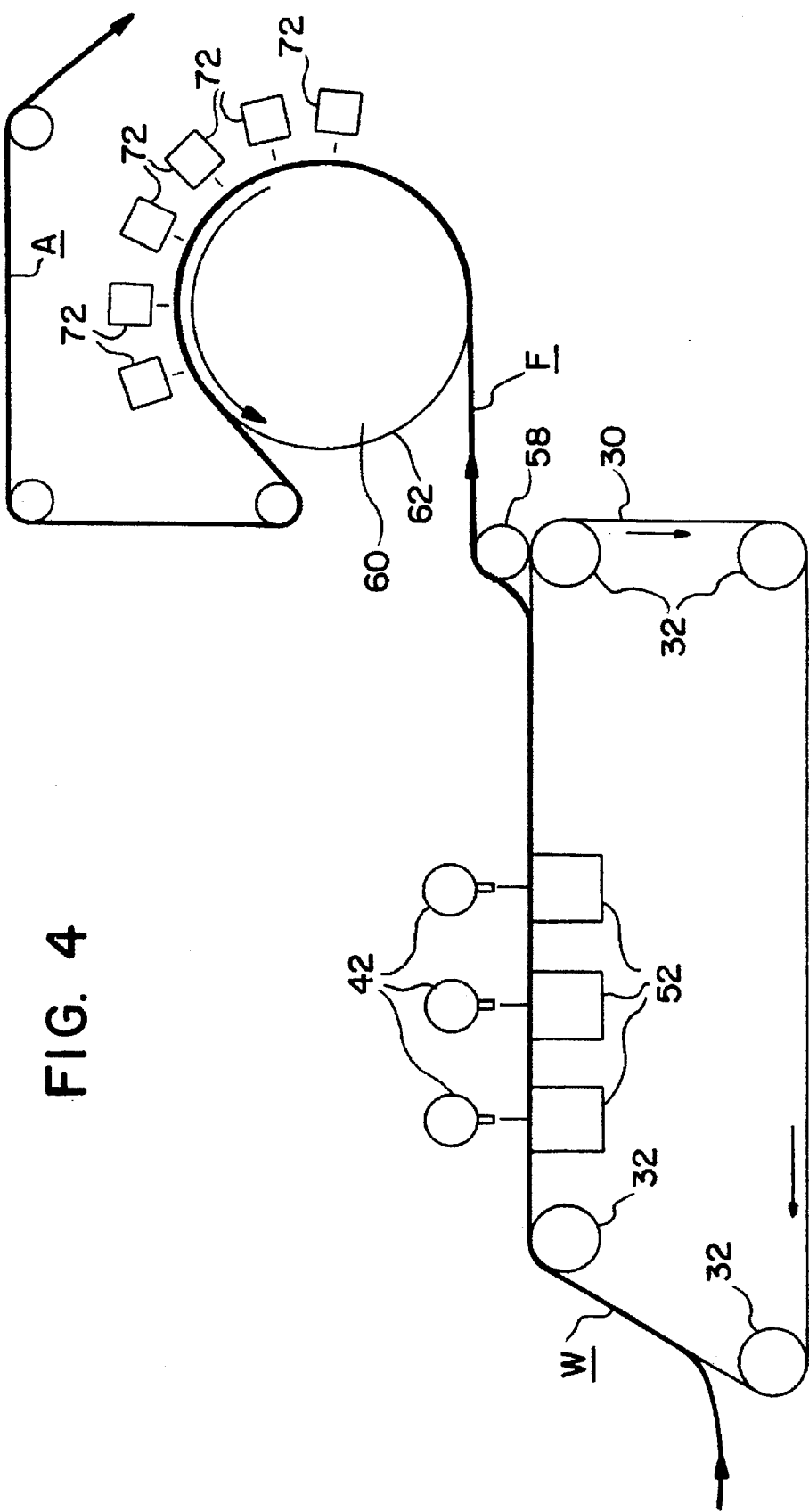
FIG. 4 is a schematic diagram of apparatus for carrying out the contemplated process diagrammed in FIG. 3.
Figure 5:
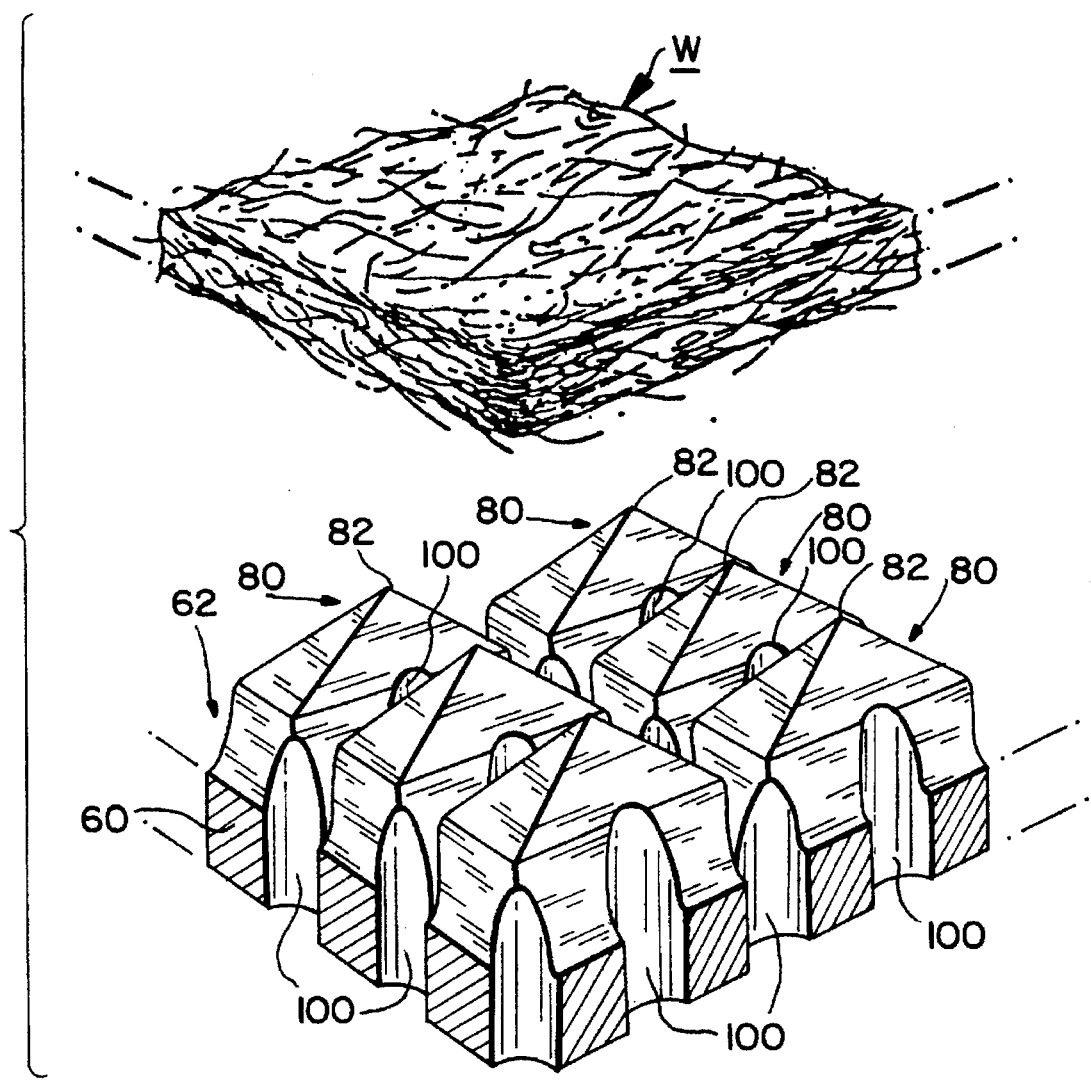
FIG. 5, on a greatly enlarged scale compared to FIG. 1, is an exploded, fragmentary, perspective view of a fibrous web and a support member having an aperture-forming surface, as used to make such an apertured fabric.
Figure 7:
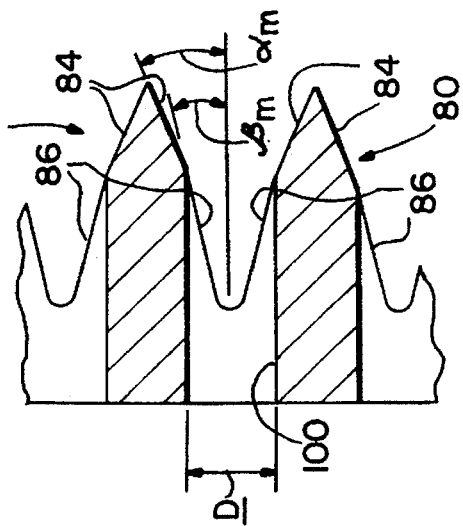
FIG. 7 is a sectional view taken along line 7—7 of FIG. 6, in a direction indicated by arrows.
Figure 6:
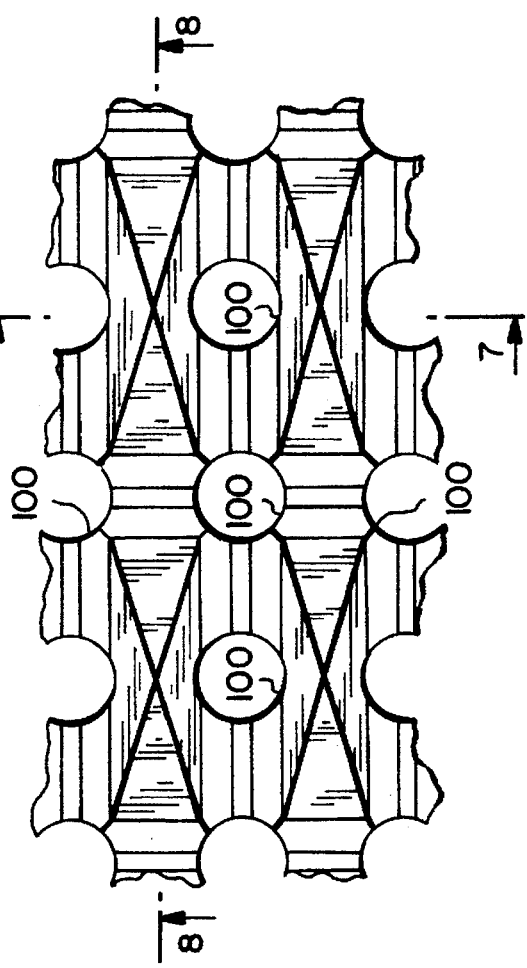
FIG. 6, on a further enlarged scale, is a plan view of a fragmentary portion of the aperture-forming surface of the support member.
Figure 8:
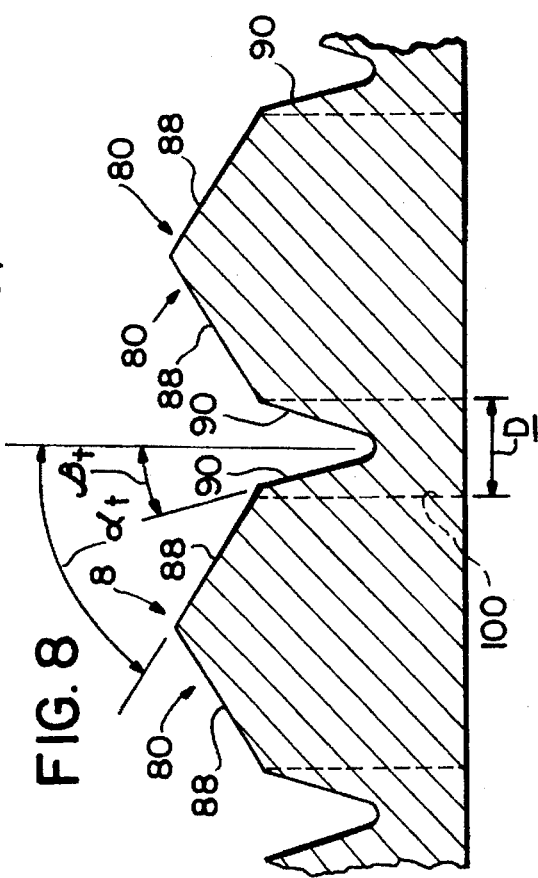
FIG. 8 is a sectional view taken along line 8—8 of FIG. 6, in a direction indicated by arrows.

FIG. 4 is a schematic diagram of a preferred apparatus for carrying out the preferred process for producing the novel, apertured, nonwoven fabric used to make sponges according to this invention.

As shown in FIG. 4, a first entangler comprises a foraminous support member, which is a conveyor belt 30 made of 100 mesh woven wire. The belt 30 is continuously moved, over conventional rollers 32, in a clockwise direction as shown. Disposed above the belt 30 is a plurality of orifice manifolds 42 to which a fluid, preferably water, is fed by a fluid-feeding manifold (not shown). Three such orifice manifolds 42 are shown in FIG. 4. Each orifice manifold 42 comprises at least one longitudinally extending row of very small diameter orifices, there being 30 or more such orifices per lineal inch. The diameter of the orifices may be in the range of 0.005 inch to 0.010 inch. The fluid-feeding manifold is connected to each of the orifice manifolds 42 by suitable piping (not shown). Each orifice manifold 42 is equipped with a pressure gauge (not shown) and a control (not shown) for regulating the pressure of the fluid in said orifice manifold. A plurality of suction members 52 is provided beneath belt 30, with one such member 52 being disposed beneath each orifice manifold 42 as illustrated in FIG. 4. A suction manifold (not shown) is connected by suitable piping to the suction members 52. The suction member and suction manifold serve to remove spent processing fluid after it has passed through the starting fibrous web W and the woven wire forming belt 30.

The fibrous web W to be formed into the nonwoven fabric is fed onto the woven wire belt 30. Water is sprayed through a nozzle (not shown) onto the fibrous web W to pre-soak or pre-wet such web W and to aid in controlling the fibers as they pass under the orifice manifolds 42. A suction slot (not shown) is placed beneath this water nozzle to remove excess water. The fibrous web W passes under the orifice manifolds 42, which are preferably operated at progressively increasing pressures. Water is the preferred fluid. As an example, the orifices of the first orifice manifold may supply fluid at pressures of 100 psig, while the orifices of the next orifice manifold supply fluid at pressures of 400 psig, and the orifices of the last orifice manifold supply fluid at pressures of 800 psig. The number of lines or rows of orifices is not critical but depends upon such factors as the weight of the fibrous web to be processed, the pressures that are used, and the number of orifices in each orifice row. After passing between orifice manifolds 42 and suction members 52, the formed fabric F is passed over an additional suction slot (not shown) to remove excess water from the formed fabric.

As also shown in FIG. 4, the formed fabric F is fed, via a stripping roller 58, to a second entangler, which comprises a rotatable drum 60. The drum 60 is rotated continuously, in a counterclockwise direction as shown. The outer, aperture-forming surface 62 of the drum 60 is a support surface, which defines the topographical configuration that is desired. A fluid-feeding manifold (not shown) is disposed adjacent to a portion of the drum periphery. The fluid-feeding manifold is connected by suitable piping to a plurality of orifice manifolds 72, each such orifice manifold 72 containing one or more rows of orifices for applying fluid, preferably water, to the formed fabric placed on the aperture-forming surface. The diameter of the orifices may be in the range of 0.005 inch to 0.010 inch. Six orifice manifolds 72 are shown. Fluid pressure in each orifice manifold 72 is controlled by a pressure gauge (not shown) and a control valve (not shown). Fluid is applied at a low pessure from the first orifice manifold 72 to tack the formed fabric to the aperture-forming surface 62. The drum 60 is connected to a sump (not shown) on which a vacuum is applied to aid in removing excess water so as to keep the forming area from flooding. The aperture-forming surface 62 with the formed fabric F thereon is passed under the remaining orifice manifolds, which apply fluid at higher pressures so as to form multiple apertures in the formed fabric F. The apertured fabric A then passes over a section of the outer drum surface where there are no orifice manifolds applying fluid to the fabric but where vacuum continues to be applied so as to de-water the apertured fabric. After being de-watered, the apertured fabric A is removed from the drum 60 and is passed around a series of drying drums (not shown) which dry the fabric.

As shown in FIGS. 5 through 8, the outer, aperture-forming surface 62 of the drum 60 comprises rows of pyramids 80. To simplify the drawings, the drum curvature is not shown in FIGS. 5 through 8. The apices 82 of the pyramids 80 are aligned in two directions perpendicular to each other. The sloping surfaces of the pyramids are hereinafter referred to as "sides" and the spaces between the pyramids are hereinafter referred to as "valleys".

Each pyramid 80 has a generally rectangular base with its longer edges extending 0.125 inch from valley to valley in the machine direction (i.e extending partly around the drum periphery) and with its shorter edges extending 0.050 inch from valley to valley in the transverse direction (i.e. extending in a direction parallel to the drum axis). The drum surface 62 has eight pyramids per inch in the machine direction (around its periphery) and 20 pyramids per inch in the transverse direction. Each pyramid 80 has an apex-to-valley height of 0.065 inch. The base of each valley is radiused to 0.003 inch.

On each pyramid 80, each sloping side extending in the machine direction defines an upper surface 84 defining one side of the apex 82 of such pyramid 80 (see FIG. 8) and a lower surface 86 defining one side of the valley between such pyramid and an adjacent pyramid. As viewed in the machine direction (see FIG. 7) each upper surface 84 defines an angle $\alpha_m$ of 24° with a plane normal to the drum axis and each lower surface 86 defines an angle $\beta_m$ of 15° with a plane normal to the drum axis. On each pyramid 80, each sloping side extending in the transverse direction defines an upper surface 88 (see FIG. 8) defining one side of the apex 82 of such pyramid 80 and a lower surface 90 defining one side of the valley between such pyramid and an adjacent pyramid. As viewed in the transverse direction, each upper surface 88 defines an angle $\alpha_t$ of 56° with a plane normal to the drum axis and each lower surface 90 defines an angle $\beta_t$ of 15° with a plane normal to the drum axis.

A plurality of holes 100 extending through the drum are disposed in a regular pattern around the drum 60. The holes 100 (see FIG. 6) are disposed in the valleys, at the centers of the longer sides of adjacent pyramids 80, and where four pyramids 80 meet. Each hole 100 has a diameter D of 0.033 inch. The holes 100 at the centers of the longer sides of adjacent pyramids 80 cause the fibers being entangled to form the "bow tie" configurations of the apertured fabric A. The holes 100 where four pyramids 80 meet cause the fibers being entangled to form the junctures of such fabric A.

Description of Tables I and II

Hereinafter, Tables I and II compare minimal, preferred, and most preferred values for the fabric used to make sponges according to this invention and representative values for woven cotton gauze. Table I compares such values for Calculated Strand Density, Clarity Index, Aperture Size, and number of apertures per unit area. Table II compares such values for Absorbent Capacity, Plug Harshness, and Compression Recovery. All values in Tables I and II are approximate and subject to normal experimental error. All test procedures were performed on binder-free fabrics.

TABLE I

| Sponge Fabric of Invention | Calculated Strand Density (g/cc³) | Clarity Index | Aperture Size (mm²) | Number of Apertures per Unit Area (cm²) |
|---|---|---|---|---|
| Minimal | at least 0.11 | at least 0.4 | at least 0.6 | fewer than 77.5 |
| Preferred | at least 0.14 | at least 0.5 | at least 1.0 | fewer than 46.5 |
| More Preferred | at least 0.17 | at least 0.75 | at least 1.3 | fewer than 31 |
| Woven Gauze | 0.35 | 1.3 | 3.1 | 25 |

TABLE II

| Sponge Fabric of Invention | Absorbent Capacity (g/g at 3.3 g/cm²) | Compressive Pressure (g/cm²) | Plug Harshness Absorbent Capacity (g/g at Compressive Pressure) | Compression Recovery (g/g at 3.3 g/cm²) |
|---|---|---|---|---|
| Minimal | at least 5.0 | at least 296 | at least 2.5 | at least 4.0 |
| Preferred | at least 6.0 | at least 247 | at least 3.0 | at least 4.5 |
| More Preferred | at least 7.0 | at least 222 | at least 3.25 | at least 5.0 |
| Woven Gauze | 3.8 | 354 | 2.2 | 3.6 |

EXAMPLE 1

Using the apparatus illustrated schematically in FIG. 4, the process diagrammed in FIG. 3 and described above produces a novel, apertured, nonwoven fabric useful to make sponges according to this invention. Initially, a 50% card-50% isocard, fibrous web weighing 525 grams per square yard and comprising 5.0 micronaire, 1.0 inch staple length, bleached cotton fiber is produced by the method disclosed in Lovgren et al. U.S. Pat. No. 4,475,271, the disclosure of which is incorporated herein by reference.

In the first entangler, the forming belt is a 103×88 (nominal 100 mesh), polyester, plain weave, monofilament forming belt from Appleton Wire, Portland, Tenn. The forming belt has a warp wire diameter of 0.15 mm, a shute wire diameter of 0.15 mm, and an open area of 17.4% of the total area. The first entangler comprises six orifice manifolds 42 arranged above the forming belt in the manner generally illustrated in FIG. 4. The first orifice manifold (corresponding to the leftmost orifice manifold 42 shown in FIG. 4) has a single row of orifices, with each orifice being approximately 0.007 inch (approximately 0.018 cm) in diameter. There are 30 such orifices per lineal inch. The second orifice manifold is substantially identical to the first. The third orifice manifold (corresponding generally to the rightmost orifice manifold 42 seen in FIG. 4) has two rows of orifices, with each orifice being approximately 0.007 inch (approximately 0.018 cm) in diameter. The two rows are separated by a distance of about 2 inches (about 5.1 cm). There are 30 such orifices per lineal inch in each of the rows. The fourth, fifth and sixth orifice manifolds (none of which are illustrated in FIG. 4) comprising the first entangler are substantially identical to the above-described third orifice manifold.

The aforementioned fibrous web is placed on the forming belt 30, wetted with water to tack the web on the forming belt 30, and passed under the six orifice manifolds just described at a rate of 100 yards per minute (91.4 meters per minute). As the fibrous web on the forming belt 30 passes under the orifice manifolds, the orifices of the first manifold supply water at a pressure of 100 psig, the orifices of the second manifold supply water at a pressure of 400 psig, and the orifices of the remaining four orifice manifolds supply water at a pressure of 800 psig. The suction members and suction manifold are maintained at a vacuum of 25 inches (63.5 cm) of water. The fibrous web is thus converted into a formed nonwoven fabric F to be further processed by means of the second entangler.

The formed fabric F from the first entangler is presented to the second entangler such that the side previously in contact with the upper surface of the forming belt 30 is exposed to direct contact with the ejected water, and the side that was exposed to direct contact with the ejected water in the first entangler is now in direct contact with the forming surface of the second entangler.

In the second entangler, the rotatable drum has an outer, topographical, aperture-forming surface substantially identical to the aperture-forming surface shown in FIGS. 5 through 8 and described above. The second entangler utilizes five orifice manifolds 72 arranged in the manner shown generally at the right-hand side of FIG. 4. The first orifice manifold encountered by formed fabric F as it travels around drum 60 of the second entangler comprises a single row of orifices, with each orifice being approximately 0.007 inch (approximately 0.018 cm) in diameter. The row of orifices has 30 orifices per lineal inch. The second orifice manifold encountered by fabric F comprises two rows of orifices, with each orifice being approximately 0.007 inch (approximately 0.018 cm) in diameter. The two rows are separated by a distance of about 2 inches (about 5.1 cm). There are 30 such orifices per lineal inch in each row of orifices. The third, fourth and fifth orifice manifolds of the second entangler are substantially identical to the above-described second orifice manifold.

The formed fabric F from the first entangler is first wetted with water to position the web on the aperture-forming surface 62 and is then passed under the aforementioned orifice manifolds 72 at a rate of 100 yards per minute (91.4 meters per minute). As the formed fabric F on the drum surface is passed under the orifice manifolds, the orifices of the first orifice manifold supply water at a pressure of 400 psig and the orifices of the remaining four orifice manifolds supply water at a pressure of 1600 psig. The sump to which the drum is connected is maintained at a vacuum of 25 inches (63.5 cm) of water. After being subjected to the water ejected from the five orifice manifolds, the fabric is dewatered over a vacuum slot, dried and rolled up to await further processing. The formed fabric exiting the first entangler is thus converted into an apertured fabric A useful to make sponges according to this invention.

EXAMPLE 2

An apertured fabric useful to make sponges according to this invention is made using the apparatus and process described in conjunction with Example 1, except that the drum 60 is not used. Rather, a foraminous forming belt is used as the support member of the second entangler. The forming belt is a 12×14 (nominal count) polyester monofilament, plain weave belt, Type 12C from Appleton Wire, Portland, Tenn. and has an open area of 38.5%. The forming belt has a warp wire diameter of 0.028 inch (0.71 mm) and a shute wire diameter of 0.030 inch (0.76 mm).

EXAMPLE 3

An apertured fabric useful to make sponges according to this invention is made using the apparatus and process described in conjunction with Example 1, except that certain processing conditions and the number of orifice manifolds employed are changed. Seventeen (17) orifice manifolds are employed, each manifold having a single row of orifices of the size and spacing mentioned in Example 1. The fibrous web is placed on the forming belt of the first entangler, wetted with water to position the web on the forming belt, and passed under the orifice manifolds associated therewith. The fibrous web is passed under the orifice manifolds (while water is being ejected therefrom) at a rate of 100 yards (91.4 meters) per minute. Water is supplied to the orifices of the first orifice manifold at a pressure of 100 psig. Water is supplied to the orifices of the next manifold at a pressure of 400 psig. The fibrous web is then passed beneath the remaining fifteen orifice manifolds to which water is supplied at a pressure of 1000 psig. The suction manifold is maintained at a vacuum of 40 inches (101.6 cm) of water.

Sixteen (16) orifice manifolds are employed in the second entangler, each such manifold having a single row of orifices of the size and spacing set forth in Example 1. Water is supplied to the first orifice manifold at a pressure of 400 psig. Water is supplied to the remaining fifteen (15) orifice manifolds at a pressure of 2000 psig. The suction manifold is maintained at a vacuum of 40 inches (101.6 cm) of water. The fabric is passed at a rate of 100 yards per minute (91.4 meters per minute).

Description of Tables III and IV

Hereinafter, Tables III and IV compare the Absorbent Capacity, Clarity Index, and Calculated Strand Density for samples of fabric made in accordance with the foregoing Examples. Table III sets forth certain of such values for replicate test specimens taken from a representative sample of fabric made in accordance with Example 1. Table IV sets forth such values for samples of fabrics made in accordance with Examples 2 and 3. All values in Tables III and IV are approximate.

Absorbent Capacity for replicate test specimen 02 was determined to be 7.7 grams per gram of the fabric, at a pressure of 3.3 grams per square centimeter, as determined in accordance with the test procedure set forth hereinafter.

TABLE III

| Example 1 Replicate Test Specimens | Calculated Strand Density (g/cm$^3$) | Clarity Index |
| --- | --- | --- |
| 01 | 0.164 | 0.76 |
| 02 | 0.154 | 0.66 |
| 03 | 0.141 | 0.57 |
| 04 | 0.152 | 0.43 |
| 05 | 0.146 | 0.69 |
| 06 | 0.140 | 0.60 |
| 07 | 0.162 | 0.60 |
| 08 | 0.146 | 0.67 |
| 09 | 0.141 | 0.65 |
| 10 | 0.165 | 0.64 |
| 11 | 0.131 | 0.69 |
| 12 | 0.177 | 0.72 |
| mean | 0.154 | 0.66 |
| standard deviation | 0.014 | 0.04 |

TABLE IV

| Sample | Absorbent Capacity (g/g at 3.3 g/cm$^2$) | Calculated Strand Density (g/cm$^3$) | Clarity Index |
| --- | --- | --- | --- |
| Example 2 | 7.1 | 0.114 | 0.40 |
| Example 3 | 8.1 | 0.197 | 0.88 |

Determination of Absorbent Capacity and Other Parameters

Absorbent Capacity, Plug Harshness, and Compression Recovery are determined by means of a gravimetric absorbency tester according to Krainski U.S. Pat. No. 4,332,175 and McConnell U.S. Pat. No. 4,357,827, the disclosures of which patents are incorporated herein by reference. A colored, aqueous, saline solution is used, which is specified as comprising approximately 1.0% by weight sodium chloride and approximately 0.025% by weight Sandolan Rhodamine EB (Xanthene dye).

Generally, the gravimetric absorbency tester comprises a vessel for containing liquid, the vessel being supported on a balance, an indicator for indicating the weight sensed by the balance, a test surface to receive a specimen to be tested, the test surface including a test site, a conduit operatively connecting the vessel to the test site for directing a flow of liquid between the vessel and the test site, and an adjuster for vertically positioning the test site with respect to the liquid level in the vessel. The vessel is supported by a spring affixed to the balance, which serves to maintain the surface of the liquid in the vessel at a constant elevation as liquid flows into and out of the vessel. The gravimetric absorbency tester is used to determine the weight of liquid flowing between the vessel and the test site and being absorbed or exorbed by a specimen when the specimen is compressed under a given, controllable, equilibrium pressure.

A stacked sample of multi-ply sponges (twelve-ply in the case of sponges of woven cotton gauze and four-ply in the case of sponges according to this invention) is prepared as follows:

1. Ten multi-ply sponges are placed on top of each other, each oriented in the same direction, to form a stack of sponges.
2. By means of a Carver Press, a 2-inch diameter test sample is die-cut from the stack of sponges.
3. The height of the die-cut stack is adjusted, if necessary, by adding additional layers or removing excess layers of material so that the stack fits under the pressure foot described hereinafter.
4. The die-cut stack is weighed and its weight is recorded.

The stacked sample is tested by means of the gravimetric absorbency tester, a load-thickness module, a pressure foot, a strip chart recorder, and other standard equipment as follows:

5. The pressure foot is centered over the multi-point plate holes of the gravimetric absorbency tester.
6. Recorder pens are placed in the down position.
7. Chart paper advance is initiated.
8. The load-thickness module is started.
9. The stacked sample under test is allowed to come to a dry thickness equilibrium under a 67 gram load which provides a pressure of 3.3 grams per square centimeter.
10. The sample is then allowed to absorb the test liquid (contained in the reservoir), which is the colored, aqueous, saline solution specified herein.
11. The sample is allowed to come to a wet Absorbent Capacity and thickness equilibrium under the same load providing the same pressure as in 9. above. The equilibrium wet thickness is noted.
12. One half of the equilibrium wet thickness is calculated.
13. The pressure provided by the pressure foot is gradually increased until the sample has been compressed to a thickness, $x_{cm}$, defined by the following formula:

$$x_{cm} = \frac{1}{2}(EWT + 1.0 \text{ cm})$$

where EWT is the equilibrium wet thickness in centimeters. The sample continues to decrease in thickness.

The sample is allowed to settle and a final pressure adjustment is made until target thickness, i.e., one half of the equilibrium wet thickness, is achieved.

14. The sample is allowed to equilibrate under the finally adjusted pressure, which is recorded as it cannot be obtained from the chart tracing.
15. Once the sample has equilibrated, the pressure is quickly and immediately adjusted until a 67 gram load providing a pressure of 3.3 grams per square centimeter has been achieved.

At the completion of the test (end of Step 15), the weight of test liquid absorbed at the end of Step 11, the weight of test liquid absorbed under the Compressive Pressure at the end of Step 14 and the weight of the test liquid absorbed at the end of Step 15 are read from the strip chart. These values are then divided by the weight recorded in Step 4 to obtain absorptive capacities in grams of test liquid per gram of fabric tested.

Determination of Clarity Index

Image analysis specified for determining the Clarity Index of an unbonded apertured nonwoven fabric is next described. Clarity Index is measured on apertured nonwoven fabrics that contain no binder. Clarity of an apertured fabric is a function of the fiber distribution in a fabric with the Clarity Index increasing as a greater portion of the fiber is placed in distinct Fiber Cover areas which surround apertures in the fabric.

To determine the Clarity Index of an unbonded apertured fabric, several area fractions are measured. Fiber Cover (FC) is the area fraction representing the yarns of woven gauze, for example, or the distinct fiber bundles of apertured nonwovens. Fiber in Apertures (FA) is the area fraction representing fiber which is not in the fiber bundles but intrudes into the open spaces between yarns of woven gauze, for example, or into the apertures of nonwoven fabrics. Cleared Apertures Area Fraction (CA) represents the area fraction of the openings or apertures in the fabric [the sum of the Open Area (OA) area fraction and the FA area fraction]. The Clarity Index (CI) of an apertured fabric is calculated as the ratio of the Cleared Apertures Area Fraction (CA) to the sum of Fiber in Apertures (FA) and the Fiber Cover (FC) by the following formula:

$$CI = CA/(FA + FC)$$

The resultant Clarity Index increases with clarity of formation of the apertured fabric.

The Clarity Index of apertured fabrics may be measured by image analysis. Essentially, image analysis involves the use of computers to derive numerical information from images. The fabric is imaged through a microscope set at a magnification such that several repeat patterns are imaged on the screen while simultaneously allowing visualization of individual fibers in the fabric. The optical image of the fabric is formed by a lens on a video camera tube and transformed into an electronic signal suitable for analysis. A stabilized transmitted light source is used on the microscope in order to produce an image on the monitor of such visual contrast that the fiber covered areas are various shades from grey to black and the open or fiber-free areas are white. Each line of the image is divided into sampling points or pixels for measurement.

The Mean Aperture Area may also be determined by image analysis as the mean value of individual areas, in square millimeters, which represent the apertures surrounded by fiber covered areas identified as the Fiber Cover (FC) area.

Such analyses are carried out by using a Leica Quantimet Q520 Image Analyzer equipped with grey store option and version 4.02 software, all available from Leica, Inc. of Deerfield, Ill, USA. The light microscope used is an Olympus SZH Microscope set at a magnification of 10× by using a 0.5× objective and a dial setting of 20×. The microscope is equipped with a stabilized transmitted light source. A Cohu Model 4812 Video Camera provides the link between the microscope and the image analyzer.

Figure 9A:
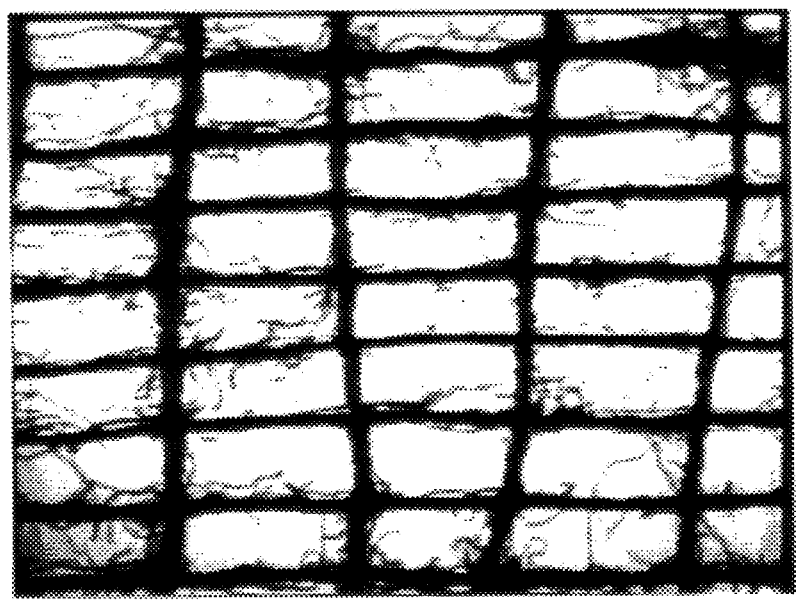
FIGS. 9A through 9F respectively are photomicrographs of a fabric under test at serial stages in image analysis of the fabric to determine the clarity of the fabric apertures.

A commercially available woven gauze fabric of U.S.P. Type VII is suitable as a reference for purposes of image analyzer set-up. The package of woven gauze is opened and a single sponge removed and unfolded to a single layer thickness. The woven gauze layer is placed between two clean glass slides on the microscope stage and sharply imaged on the video screen. The fabric pattern is oriented so that several whole pattern repeats are visible on the screen. See FIG. 9A. Using the Leica Quantimet Q520 Image Analyzer configured with an Olympus SZH Microscope, with magnification set as described above, results in an analyzer calibration of 0.021 mm/pixel and allows analysis of an area containing from 14 to 24 whole pattern repeats of the U.S.P. Type VII gauze in a single field. The image brightness and contrast (Gain and Offset) are set to include the complete range of grey levels in the displayed image (a display of the Grey Level Histogram contains all possible grey levels on scale). Such a setting allows detection of the yarns, the clear aperture areas, and the fibers extending from the yarns into the aperture areas. Next, the sample is removed from the microscope stage and the two clean glass slides are used to perform a Shading Correction to eliminate any uneven lighting across the field of view. The sample is then replaced on the microscope stage.

Figure 9B:
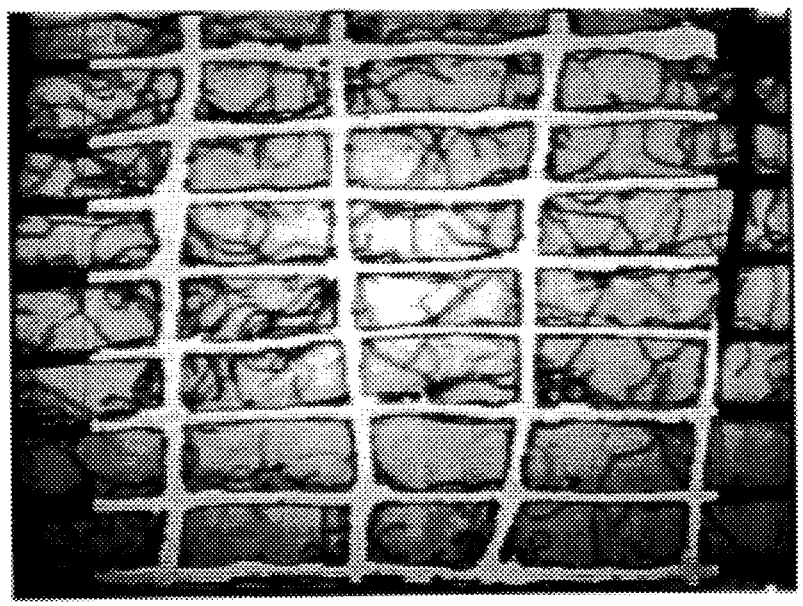

To measure the Clarity Index, several imaging operations are performed, as follows:

1. First, the black image area detect level is set to equal the bundled fiber strands and interconnected junctures only without detecting the individual fibers extending from the yarns into the apertures. See FIG. 9B. The Black Detect grey level value is noted for future reference.

Figure 9C:
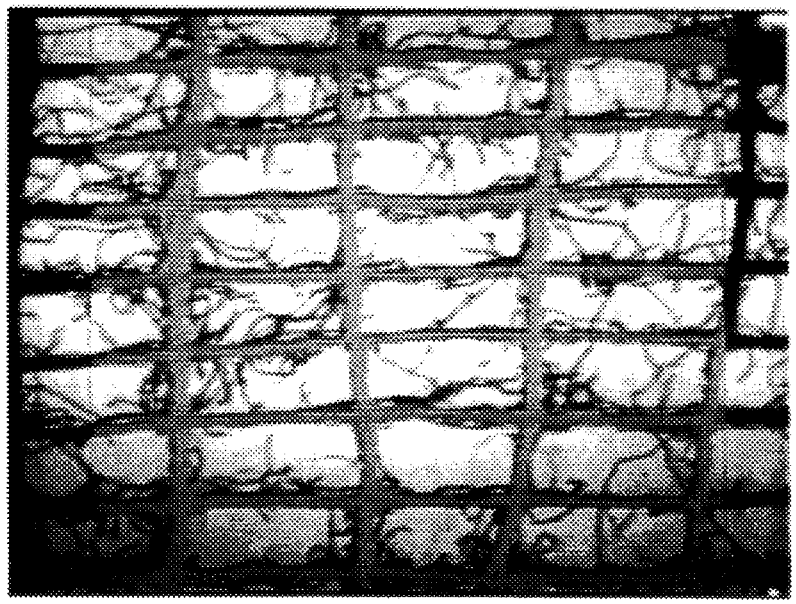

2. Using the Amend function, the detected image of the yarns in the detected Plane 1 is stored in Image Plane 3 for measurement at a later time. This image in Image Plane 3 represents the Fiber Cover area (FC). See FIG. 9C. Note: If necessary, in order to fully detect the Fiber Cover area, the image in Plane 1 is Dilated a number of cycles until holes within the Fiber Cover area are eliminated; then, the image is Eroded the same number of cycles to return Fiber Cover area edges to the original limits as set in the Detect menu.

Figure 9D:
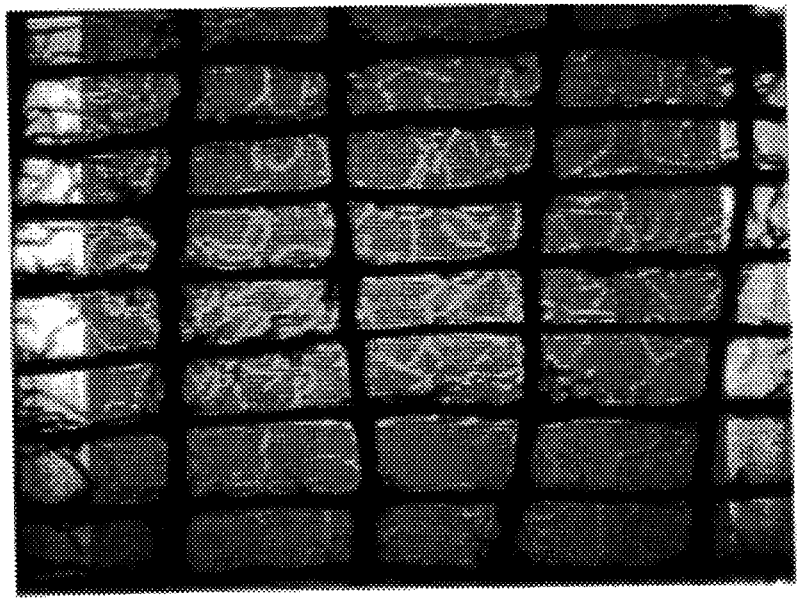

3. Next, the White Detect level is set to equal the areas that are free of fiber within each aperture in the field of view. The White Detect level is also noted for future reference. This detected image in Image Plane 1 represents the Open Area (OA) of the fabric. See FIG. 9D.

4. Using the Logical function, the images in Plane 1 and Plane 3 are combined according to the formula: Invert (Plane 1 XOR Plane 3). That is, create an image of all pixels that are not in either Plane 1 or Plane 3. This operation generates an image in Image Plane 4 of the fiber extending from the yarns into the fabric apertures or "Fiber in Apertures" (FA). See FIG. 9E.

Figure 9E:
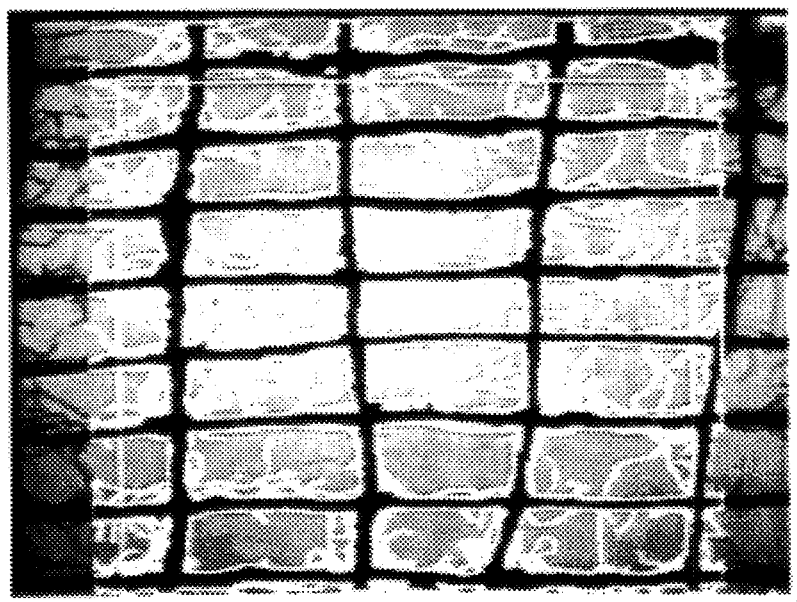

5. The following image Field Measurements are made and the Area Fraction values recorded for calculation of the Clarity Index:

Plane 1 (OA) (FIG. 9D)
Plane 3 (FC) (FIG. 9C)
Plane 4 (FA) (FIG. 9E)

A Cleared Apertures Area Fraction (CA) is calculated as the sum of the Open Area (OA) and the Fiber in Apertures (FA). The Clarity Index (CI) is also calculated as the ratio of the Cleared Aperture Area Fraction (CA) to the sum of the two area fractions, the Fiber in Apertures (FA) and the Fiber Cover (FC):

$CI=CA/(FA+FC)$.

Additional fields of the woven gauze are measured in the same manner using the Black Detect level and White Detect level chosen in steps 1 and 3. Results from a number of representative areas of the fabric (at least ten fields are analyzed for each fabric) are averaged to provide a Mean Clarity Index.

Figure 9F:
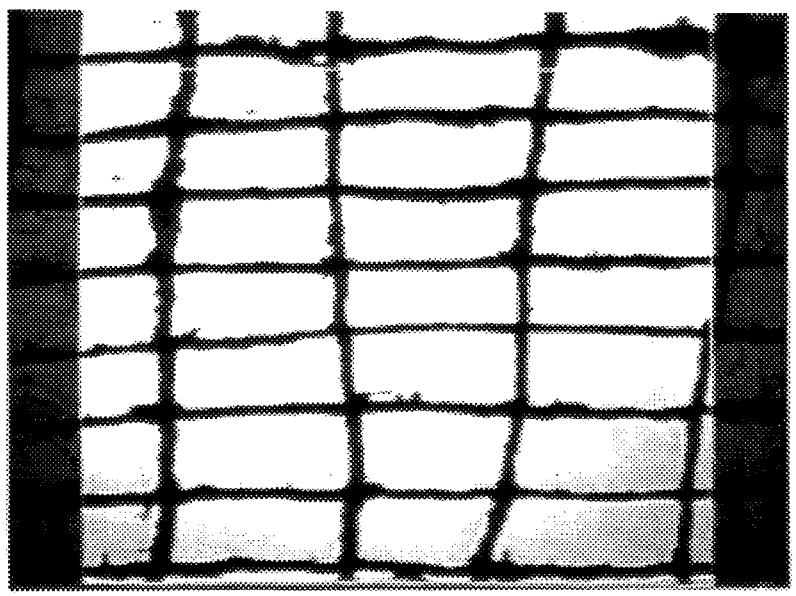

Image analysis is also used to determine the Aperture Size, as the mean aperture area in square millimeters. For each field examined in steps 1 through 5, the following steps are taken after recording the field measurements and before moving the fabric to the next field:

6. Using the Logical Function again, combine the images of Plane 1 (OA) (FIG. 9D) and Plane 4 (FA) (FIG. 9E) through the image addition (OR) function to form an image of the Cleared Apertures Area Fraction (CA) in Plane 5. See FIG. 9F. The image equation is:

Plane 5 (CA)=Plane 1 (OA) OR Plane 4 (FA).

7. In the Feature Measurement Menu, set parameters to measure Plane 5 (CA).

8. In the Histogram Menu, choose the Area parameter and highlight this as the graph choice. Then, choose Measure to analyze the image of Plane 5, CA, for individual feature areas.

9. Repeating steps 6 through 8 for each field after the analysis for Clarity Index (steps 1 through 5, above) will generate a cumulative histogram of CA areas with Mean and Standard Deviation values (the histogram is not cleared between different fields of the same fabric sample).

10. At the end of the series of fields for the woven gauze fabric, the Aperture Area Mean and Standard Deviation, in square millimeters, are recorded.

The Clarity Index and Mean Aperture Area for fabrics used to make sponges according to this invention and fabrics according to the prior art are analyzed in a similar manner using the detect levels determined during analysis of the woven gauze. For Clarity Index, the field measurements are stored and results calculated, for example, in a Lotus 1-2-3 worksheet. The Clarity Index of each fabric is reported as the Mean Clarity Index. After accumulation of the feature data for each field, the mean and standard deviation are recorded in the worksheet and reported as the Mean Aperture Area.

Determination of Calculated Strand Density

The Calculated Strand Density refers to the density of the fiber bundles in the unbonded apertured fabric of the sponge. The Calculated Strand Density is determined from the area fraction representing the fiber covered pattern area and a fabric density calculated using the fabric weight in grams per square centimeter divided by the average thickness, in centimeters, of the fiber bundles. The measurements for determining Calculated Strand Density are made on unbonded nonwoven fabric. The method for determining the Calculated Strand Density, which is expressed in grams per cubic centimeter, for apertured nonwoven fabrics is next described.

The analysis requires determination of the fabric weight (WT) in grams per square centimeter (g/cm²), measurement of the thickness (Z) of the fiber bundles in centimeters (cm) and Clarity Index analysis to obtain the area fraction (FC) which represents the fiber covered pattern area.

A standard test method, such as ASTM D-3776, is used to determine the fabric weight. The thickness of the fiber bundles can be determined using a Leica Quantimet Q520 Image Analyzer to measure cross sections through fiber bundles.

To prepare a fabric for image analysis of the fiber bundle thickness, a representative sample of the fabric is embedded in a transparent resin (e.g. Araldite™ Resin) and cross sections of the fabric/resin block are made using a low speed saw, such as a Buehler Isomet Saw, equipped with a diamond blade. Serial cross sections, each 0.027 cm. thick, are cut in both the machine and cross directions of the fabric and mounted on glass microscope slides with, for example, Norland Optical Adhesive 60 as a mounting medium. From microscopical examination of the serial sections compared to a piece of the original fabric being analyzed, cross sections representing the fiber bundles are marked for measurement. Sections of fiber bundles in the nonwoven fabric of the sponge 10 are selected with the cut made in the region approximately midway between the "bow tie" configuration and an interconnected juncture or, when no "bow tie" configuration is present, between two interconnected junctures. Sections of fiber bundles in nonwoven fabrics of the prior art are selected with the cut made approximately midway between interconnected junctures.

The thickness of each fiber bundle selected is identified as the length of a line drawn through the cross section from the boundary representing one surface of the fabric to the boundary representing the opposite surface. The length of the lines representing each yarn bundle thickness is measured and the mean yarn bundle thickness (Z), in centimeters, is recorded. The area fraction (FC) representing the sample fiber covered pattern area is obtained from the Clarity Index analysis.

Next, the Calculated Strand Density expressed in grams per cubic centimeter (g/cc) is calculated according to the following formula:

$$\text{Calculated Strand Density} = WT/(Z \times FC)$$

Determination of Fabric Density

A method for the determination of the Fabric Density of an apertured, nonwoven fabric is next described. The Fabric Density is a value calculated from the fabric weight per unit area in grams per square centimeter, the fabric thickness in centimeters, and the area fraction representing the fabric covered pattern area in the fabric. The units of Fabric Density are grams per cubic centimeter.

Standard test methods (e.g. ASTM D-1777 and D-3776) are used to measure the weight per unit area and the thickness. Fabric bulk is then calculated by dividing the weight per unit area by the thickness and is expressed in grams per cubic centimeter. The area fraction representing the fiber covered pattern area in the fabric is the Fiber Cover (FC) value obtained from the Clarity Index analysis. See above. Next, the Fabric Density is calculated by dividing the fabric bulk by the area fraction (FC).

Conclusion

Various modifications may be made in the preferred embodiment described above, and in the processes and apparatus described above, without departing from the scope and spirit of this invention.

What is claimed is:

1. A debridement sponge made from a nonwoven fabric comprising yarn-like strands of fibers selected from the group consisting of hydrophilic fibers and blends of hydrophilic fibers and hydrophobic fibers, said strands being interconnected at multiple junctures to form multiple apertures, wherein each aperture has an area of at least 0.6 square millimeters and wherein said apertures number fewer than 77.5 per square centimeter said fabric having a Calculated Strand Density of at least 0.11 grams per cubic centimeter, said fabric having a Clarity Index of at least 0.4, and said fabric having an Absorbent Capacity of at least 5 grams of an aqueous saline solution per gram of said fabric when compressed under a pressure of 3.3 grams per square centimeter wherein said aqueous saline solution comprises approximately 1.0% by weight of sodium chloride and approximately 0.025% by weight of a xanthene dye.

2. The debridement sponge of claim 1 wherein said apertures are generally rectangular.

3. The debridement sponge of claim 1 wherein said fabric has an initial wet thickness determined when said fabric is compressed under a pressure of 3.3 grams per square centimeter, said fabric having a Plug Harshness such that said fabric is compressible under a higher pressure less than 296 grams per square centimeter to a thickness equal to approximately one half of its initial wet thickness and such that said fabric when compressed under the higher pressure has an Absorbent Capacity of at least 2.5 grams per gram of said fabric.

4. The debridement sponge of claim 3 wherein said fabric has a Compression Recovery such that, after the higher pressure is released, said fabric has an Absorbent Capacity of at least 4.0 grams per gram of said fabric when compressed under a pressure of 3.3 grams per square centimeter.

5. The debridement sponge of claim 1 wherein the strand fibers are bleached cotton fibers.

6. A debridement sponge made from a nonwoven fabric comprising yarn-like strands of fibers including hydrophilic fibers, said strands being interconnected at junctures to form generally rectangular apertures, wherein each aperture has an area of at least 1.0 square millimeters and wherein said apertures number fewer than 46.5 per square centimeter, said fabric having a Calculated Strand Density of at least 0.14 grams per cubic centimeter, said fabric having a Clarity Index of at least 0.5, said fabric having an Absorbent Capacity of at least 6 grams of an aqueous saline solution per gram of said fabric when compressed under a pressure of 3.3 grams per square centimeter wherein said aqueous saline solution comprises approximately 1.0% by weight of sodium chloride and approximately 0.025% by weight of a xanthene dye.

7. The debridement sponge of claim 6 wherein said fabric has an initial wet thickness determined when said fabric is compressed under a pressure of 3.3 grams per square centimeter, said fabric having a Plug Harshness such that said fabric is compressible under a higher pressure less than 247 grams per square centimeter to a thickness equal to approximately one half of its initial wet thickness and such that said fabric when compressed under the higher pressure has an Absorbent Capacity of at least 3 grams per gram of said fabric.

8. The debridement sponge of claim 7 wherein said fabric has a Compression Recovery such that, after the higher pressure is released, said fabric has an Absorbent Capacity of at least 4.5 grams per gram of said fabric when compressed under a pressure of 3.3 grams per square centimeter.

9. The debridement sponge of claim 6 wherein the strand fibers are selected from the group consisting of hydrophilic fibers and blends of and hydrophobic fibers.

10. The debridement sponge of claim 9 wherein the strand fibers are bleached cotton fibers.

11. A debridement sponge made from a nonwoven fabric comprising yarn-like strands of fibers selected from the group consisting of hydrophilic fibers and blends of hydrophilic fibers and hydrophobic fibers, said strands being interconnected at junctures to form apertures, said fabric having a Calculated Strand Density of at least 0.17 grams per cubic centimeter, said fabric having a Clarity Index of at least 0.75, said fabric having an Absorbent Capacity of at least 7 grams of an aqueous saline solution per gram of said fabric when compressed under a pressure of 3.3 grams per square centimeter wherein said aqueous saline solution comprises approximately 1.0% by weight of sodium chloride and approximately 0.025% by weight of a xanthene dye, wherein said fabric has an initial wet thickness determined when said fabric is compressed under a pressure of 3.3 grams per square centimeter, said fabric having a Plug Density such that said fabric is compressible under a pressure less than 222 grams per square centimeter to a thickness equal to approximately one half of its initial wet thickness and such that said fabric when compressed under the higher pressure has an Absorbent Capacity of at least 3.25 grams of said aqueous saline solution per gram of said fabric.

12. The debridement sponge of claim 11 wherein said apertures are generally rectangular.

13. The debridement sponge of claim 12 wherein each aperture has an area of at least 1.3 square millimeters and wherein said apertures number fewer than 31 per square centimeter.

14. The debridement sponge of claim 11 wherein said fabric has a Compression Recovery such that, after the higher pressure is released, said fabric has an Absorbent Capacity of at least 5.0 grams per gram of said fabric when compressed under a pressure of 3.3 grams per square centimeter.

15. The debridement sponge of claim 11 wherein the strand fibers are bleached cotton fibers.

* * * * *